United States Patent
Leger et al.

(10) Patent No.: US 10,423,017 B2
(45) Date of Patent: Sep. 24, 2019

(54) METHOD FOR DETERMINING THE CHARACTERISTICS OF A SYSTEM FOR GENERATING A SPATIAL LIGHT MODULATION IN PHASE AND AMPLITUDE AT HIGH REFRESH RATE

(71) Applicants: Institut National de la Sante et de la Recherche Medicale (INSERM), Paris (FR); Centre National de la Recherche Scientifique (C.N.R.S.), Paris (FR); Ecole Normale Superieure, Paris (FR)

(72) Inventors: Jean-Francois Leger, Sceaux (FR); Laurent Bourdieu, Paris (FR); Stephane Dieudonne, Chatenay Malabry (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); ECOLE NORMALE SUPERIEURE, Paris (FR)

( * ) Notice: Subject to any disclaimer, the term of this patent is extended or adjusted under 35 U.S.C. 154(b) by 337 days.

(21) Appl. No.: 15/517,350

(22) PCT Filed: Oct. 15, 2015

(86) PCT No.: PCT/EP2015/073883
§ 371 (c)(1),
(2) Date: Apr. 6, 2017

(87) PCT Pub. No.: WO2016/059157
PCT Pub. Date: Apr. 21, 2016

(65) Prior Publication Data
US 2017/0242281 A1    Aug. 24, 2017

(30) Foreign Application Priority Data

Oct. 15, 2014    (EP) ..................... 14306636

(51) Int. Cl.
*G02F 1/11*    (2006.01)
*G02F 1/33*    (2006.01)
(Continued)

(52) U.S. Cl.
CPC ......... *G02F 1/113* (2013.01); *G01N 21/6458* (2013.01); *G01N 21/6486* (2013.01);
(Continued)

(58) Field of Classification Search
CPC ............... G02B 21/06; G02B 21/0076; G02B 21/0036; G02B 2207/114; G02F 1/113;
(Continued)

(56) References Cited

U.S. PATENT DOCUMENTS 7,642,484 B2 * 1/2010 Gross ................... B23K 26/067
  219/121.73
10,101,634 B2 * 10/2018 Dieudonne ............... G02F 1/33
(Continued)

FOREIGN PATENT DOCUMENTS

DE   10 2013 201 968 A1   8/2014
WO       2013/102771 A1   7/2013
WO       2014/147590 A1   9/2014

OTHER PUBLICATIONS

Bechtold et al.; "Beam shaping and high-speed, cylinder-lens-free beam guiding using acousto-optical deflectors without additional compensation optics"; Optics Express, vol. 21, No. 12, Jun. 17, 2013, entire article.

*Primary Examiner* — Tuyen Tra
(74) *Attorney, Agent, or Firm* — W&C IP (57) ABSTRACT

Method for determining the characteristics of a system for generating at least one pattern of light, the method compris-
(Continued)

ing: a) providing a desired pattern of light, b) expressing the amplitude and the phase of the output pulse of the system as a function of the input laser pulse and in function of the characteristics of the system to obtain a calculated output pulse, the input laser pulse having a duration below or equal to 1 nanosecond, c) determining at least one characteristic of the system by minimizing a distance between the calculated output pulse and the desired output laser pulse.

14 Claims, 3 Drawing Sheets

(51) Int. Cl.
 *G02B 21/00* (2006.01)
 *G01N 21/64* (2006.01)
 *G02B 21/06* (2006.01)

(52) U.S. Cl.
 CPC ..... *G02B 21/0036* (2013.01); *G02B 21/0076* (2013.01); *G02B 21/06* (2013.01); *G02F 1/33* (2013.01); *G01N 2201/0675* (2013.01); *G01N 2201/06113* (2013.01); *G02B 2207/114* (2013.01); *G02F 2201/16* (2013.01); *G02F 2203/12* (2013.01)

(58) Field of Classification Search
 CPC .... G02F 1/33; G02F 2203/12; G02F 2201/16; G01N 21/6486; G01N 21/6458; G01N 2201/06113; G01N 2201/0675
 USPC .......................... 359/237, 238, 240, 285, 286
 See application file for complete search history.

(56) References Cited

U.S. PATENT DOCUMENTS 10,191,268 B2 * 1/2019 Leger ................. G02B 21/0036
2005/0263690 A1 12/2005 Akinori et al.

* cited by examiner

METHOD FOR DETERMINING THE CHARACTERISTICS OF A SYSTEM FOR GENERATING A SPATIAL LIGHT MODULATION IN PHASE AND AMPLITUDE AT HIGH REFRESH RATE

TECHNICAL FIELD OF THE INVENTION

The invention relates to a method for determining the characteristics of a system for generating at least a spatial modulation of light in phase and in amplitude. The invention also concerns to an associated computer program product. The invention also relates to a system for generating a spatial modulation of light having at least a characteristic determined by the method for determining. The invention concerns a method for generating a light pattern and a method for analyzing a sample using such system for generating a light pattern.

BACKGROUND OF THE INVENTION

In optical microscopy, the generation of patterns of light at high spatial and temporal resolution is desirable. A pattern of light refers here to the focusing of light at one or more spots at given positions in 2D and 3D and to the sculpting of the light intensity distribution in an extended pattern around these spots. Indeed, a pattern of light can be used to image the structure and activity of biological samples, such as neuronal dendrites. A pattern of light also enables to modify optically the biological activity or chemical environment of these biological samples. It is therefore desirable to be able to generate arbitrary light patterns at a high speed.

For this, it is known to carry out a three-dimensional scanning of a sample by using galvanometers for in-plane scanning and various mechanical designs for scanning along the optical axis (Z scanning). These designs include displacement of optical elements such as lenses or optically-conjugated mirrors or deformation of liquid lenses.

However, due to the poor spatio-temporal patterning capacity of both galvanometers and mechanical Z-scanning devices, the versatility of this approach is limited. It results in spatially constrained light pattern formation at a relatively low speed.

Spatially extended light patterns are also produced by devices able to spatially shape the light in phase and/or amplitude, including mainly liquid-crystal SLM (Spatial Light Modulators) and DM (Deformable Mirrors). These devices are also limited in their ability to refresh at high rate the modulation pattern, in most of the cases in the range of a few Hz to a few kHz.

In the case of the scanning in 3D of a single spot, it is also known from the article by Reddy et al. entitled "Three-dimensional random access multiphoton microscopy for functional imaging of neural activity" published in Nature neuroscience, 11, 713-720 (2008) to achieve three-dimensional ultra-fast scanning using a system involving four acousto-optic deflectors.

Acousto-optic deflectors (often named after their acronym AOD) are fast pointing devices based on the interaction between an acoustic compression or shear wave propagating in an acousto-optical crystal and an electromagnetic wave. In most cases, the electromagnetic wave has a planar or a spherical wavefront. If a fixed frequency wave is used in the AOD, the resulting diffractive process deflects a fraction of the electromagnetic wave at an angle proportional to the acoustic frequency of the acoustic wave. The use of linearly chirped wave in the AOD, as described in the article by Reddy et al., allow creating a cylindrical lens in the AOD, whose focal length is inversely proportional to the chirp rate.

The system described in this article, which contains 4 AOD, implies strong loss of light power because the diffraction efficiency in an acousto-optic deflector is limited even in its optimal configuration. In addition, the third and the fourth acousto-optic deflectors of the system cannot be used in their optimal configuration (Bragg incidence), which also contributes to increase the loss of light power in the system. Finally, the linear frequency chirps have to be stopped each time they reach the limit of the frequency bandwidth of the AOD, thus limiting the dwell time on the points accessed in 3D and the useful fraction of the duty cycle. Finally, this system is limited to the scanning in 3D of a single spot and cannot be used to create extended light patterns.

It is also known from document DE 10 2013 201 968 a device which has a radiation source generating a pulsed, electro-magnetic radiation. A photodetector is used for temporal detection of radiation pulses. A signal source is coupled with the photodetector for precise trigger of sound waves generation. An acousto-optical deflector is driven by the signal source with a frequency-modulated control signal such that sound waves and radiation are linked in time. In this implementation refractive and/or diffractive beam transformation and/or beam deflection of the radiation is/are performed at the time of passage of the radiation through the deflector.

SUMMARY OF THE INVENTION

The invention aims at solving the problems of the known systems with a new system for generating a spatial shaping of light in phase and amplitude and thus a light pattern, which is able to operate at a high speed.

To this end, the invention concerns a method for determining the characteristics of a system for generating a desired spatial light modulation in phase and in amplitude of a laser pulse, the system comprising:
  a laser unit adapted to emit at least one input laser pulse having a duration below or equal to 1 nanosecond,
  a spatial shaping unit being adapted to generate an output laser pulse when illuminated by an input laser pulse, the spatial shaping unit comprising at least one acousto-optical deflector, each acousto-optical deflector being adapted to deflect an incident laser pulse along a respective deflection direction to obtain a deflected laser pulse, each acousto-optical deflector comprising an acousto-optical crystal and a transducer adapted to command the crystal by applying an acoustic wave,
  the laser unit and the shaping unit being synchronized such that the incident laser pulse interacts with the respective acousto-optic deflector when the acoustic wave is established in the crystal,
  the method comprising:
  a) providing a desired spatial light modulation in phase and in amplitude of the output pulse,
  b) expressing the amplitude and the phase of the output pulse of the shaping unit as a function of the input laser pulse and in function of the characteristics of the system to obtain a calculated output pulse,
  characterized in that:
  the method further comprises:
  c) determining at least one characteristic of the system by minimizing a distance between the calculated output pulse and the desired output laser pulse, at step b), for each acousto-optical deflector, the phase shift introduced by the acousto-optical deflector between the deflected laser pulse and the incident laser pulse is expressed as:

$$\varphi(m) = \frac{2\pi}{v}\left(mf(m) - m_0 f(m_0) - \int_{m_0}^{m} uf'(u)du\right)$$

wherein:
φ is the phase shift introduced by the acousto-optical deflector in the incident laser pulse,
m is the coordinate of the position of a point of the acousto-optical crystal along the deflection direction,
$m_o$ is the coordinate of the position of the extremity of the acousto-optical crystal along the deflection direction and opposite to the transducer,
v is the speed of the acoustic wave applied to the crystal of the acousto-optical deflector, and
f(m) is the frequency of the acoustic wave applied to the crystal of the acousto-optical deflector at the point of coordinate m at the instant when the laser pulse crosses the crystal.

at step b), for each acousto-optical deflector, the amplitude modulation introduced by the acousto-optical deflector between the deflected laser pulse and the incident laser pulse is expressed as:

$$A(m) = T(a(m))$$

wherein:
A(m) is the amplitude modulation introduced by the acousto-optical deflector in the incident laser pulse at the point of coordinate m,
a(m) is the amplitude of the acoustic wave applied to the crystal of the acousto-optical deflector at the point of coordinate m at the instant when the laser pulse crosses the crystal, and
T is the characteristic input-output amplitude transfer function of the acousto-optical deflector expressing the fraction of the input light amplitude transferred into the first diffraction order, as a function of the acoustic wave amplitude.

Thanks to the invention, the characteristics of a system enabling to generate a spatial shaping of light in phase and amplitude at high speed are determined.

According to further aspects of the invention which are advantageous but not compulsory, the method might incorporate one or several of the following features, taken in any technically admissible combination:

the shaping unit comprises at least two acousto-optical deflectors in series, the number of acousto-optical deflectors being a characteristic of the system and being determined at step c) under the constraint that the number of acousto-optical deflectors be superior or equal to 2, preferably superior or equal to 4.

each characteristic determined at step c) is determined under the constraint that the deflection directions are equally spaced angularly.

the system further comprises a radiofrequency generator adapted to provide to each transducer radiofrequency wave starting at a respective instant, the instants being characteristics of the system and being determined at step c).

the system further comprises a laser unit adapted to emit laser pulse at emitting instants, the emitting instants being a characteristic of the system and each acousto-optic deflector has an access time, the emitting instants being determined at step c) under the constraint that the repetition rate of the laser unit be inferior or equal to the inverse of the largest of these access times.

the characteristics are chosen in the group consisting of the optical distances between the acousto-optical deflectors, the angles between the deflection directions and the number of acousto-optical deflectors.

The invention also relates to a computer program product comprising a computer readable medium, having thereon a computer program comprising program instructions, the computer program being loadable into a data-processing unit and adapted to cause execution of a method as described here above.

The invention also relates to a system for generating a desired spatial modulation in phase and in amplitude of a laser pulse, the system comprising a laser unit adapted to emit at least one input laser pulse having a duration below or equal to 1 nanosecond, a shaping unit being adapted to generate an output laser pulse when illuminated by an input laser pulse, the shaping unit comprising at least one acousto-optical deflector, each acousto-optical deflector being adapted to deflect an incident laser pulse along a respective deflection direction to obtain a deflected laser pulse, each acousto-optical deflector comprising an acousto-optical crystal and a transducer adapted to command the crystal by applying an acoustic wave. The laser unit and the shaping unit are synchronized such that the incident laser pulse interacts with the respective acousto-optic deflector when the acoustic wave is established in the crystal. The system has at least a characteristic determined by the method for determining according as described here above.

According to a preferred embodiment, the laser unit comprises a laser and a regenerative amplifier.

The invention also concerns a two-photon microscope comprising a system for generating a desired laser pulse as described here-above.

The invention also relates to a method of generating a desired spatial modulation in phase and in amplitude of a laser pulse by using the system for generating at least a desired laser pulse as described here-above.

The invention also concerns a method for analyzing or modifying a sample comprising generating a light pattern within a sample by using the method for generating at least a desired spatial modulation in phase and in amplitude of a laser pulse as described here-above.

According to an embodiment, the method comprises modifying the position of the pattern of light in the sample along a direction perpendicular to the focal plane.

According to another embodiment, the sample is adapted to tolerate an exposition to a maximum repartition of intensity of light in the focal plane and the method further comprises choosing the desired pattern of light so that the repartition of the intensity of the desired pattern of light in the focal plane be inferior to the maximum repartition of intensity.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

For the remainder of the description, a longitudinal direction is defined: the longitudinal direction corresponds to the general direction of the propagation of light. Two transversal directions perpendicular to the longitudinal direction are also defined, the first transversal direction being further perpendicular to the second transversal direction. The longitudinal and transversal directions are respectively symbolized by an axis Z and axes X and Y on FIGS. 1 to 3.

Figure 1:
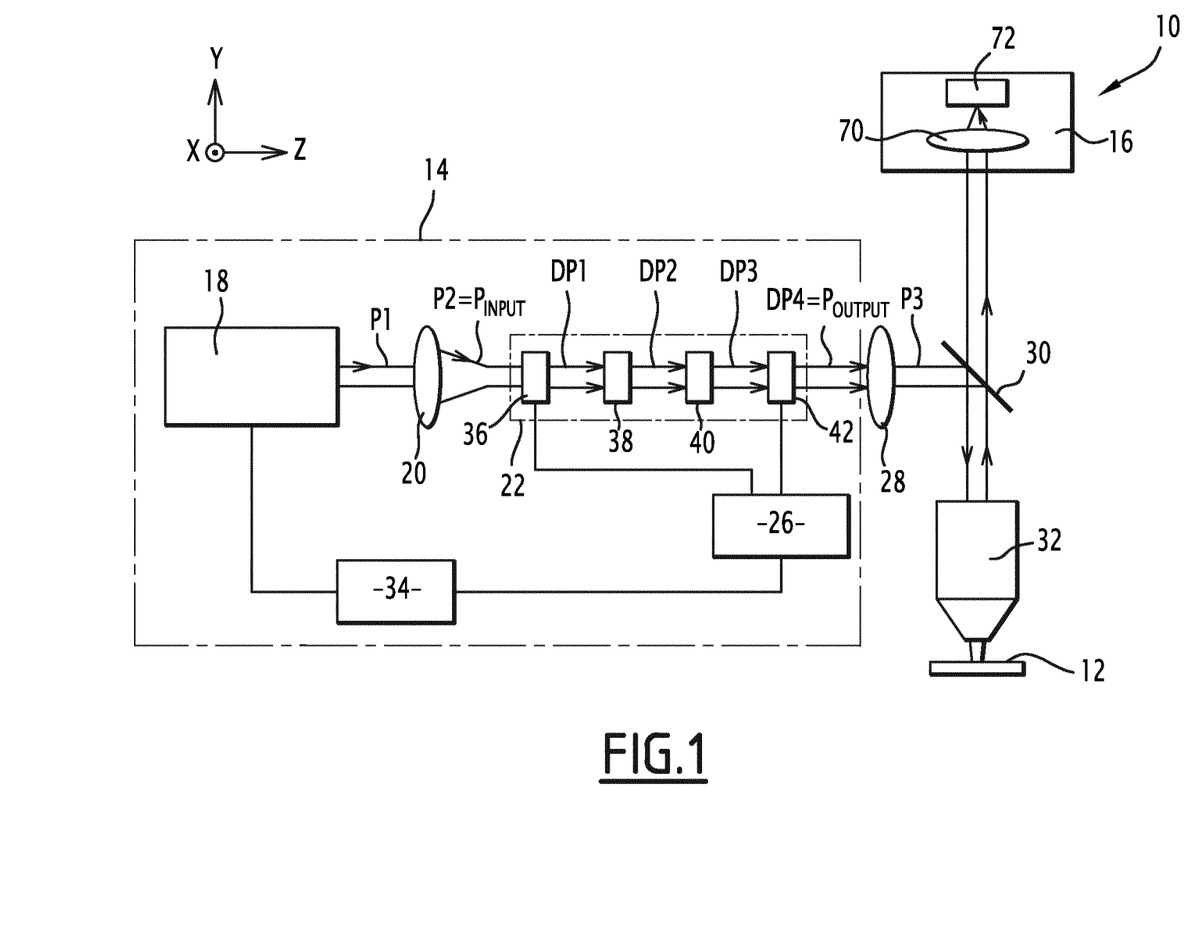
FIG. 1 is a schematic representation of a two-photon microscope according to the invention comprising a system for generating a spatial modulation of light according to the invention.

A two-photon microscope 10 adapted to achieve two-photon microscopy on a sample 12 is represented on FIG. 1.

The sample 12 is, for instance, a soft tissue. In the meaning of the present invention, a soft tissue is an organic tissue which can have an animal or vegetal origin. For instance, such a soft tissue can be a muscle or any portion of a human body, of an animal body or of a plant. A soft tissue can also be a non-metallic part of a prosthesis.

The microscope 10 comprises a system 14 for generating at least a desired spatial light modulation, which is transformed into pattern of light by as optical system 28 and by the objective 32, a beam splitter 30, and a detecting unit 16.

The system 14 for generating at least a desired spatial light modulation comprises a laser unit 18, a first optical system 20, a shaping unit 22, a radiofrequency generator 26 for the shaping unit 22, and a controller unit 34.

System 14 and the objective are adapted to generate a desired pattern of light in the sample 12. A light pattern refers here to the focusing of light in the sample 12 at one or more spots at given positions in 2D and 3D and to the sculpting of the light intensity distribution in an extended pattern around these spots. For instance, a light pattern is a square or four points arranged spatially so as to from a square.

The laser unit 18 comprises a laser source. The laser source is adapted to emit a coherent light whose wavelength is comprised between 400 nanometers (nm) and 2 micrometers (µm). The laser unit 18 is adapted to emit at least one laser pulse having a duration below or equal to 1 nanoseconde. The laser source is preferably a femtosecond pulsed laser adapted to emit laser pulses with a duration comprised between 10 fs and 10 picoseconds (ps).

Preferably, the femtosecond laser is adapted to emit laser pulses with a full width at half maximum strictly inferior to 2 picoseconds.

Alternatively, the laser unit 18 also comprises an element of spatial and/or temporal precompensation of the pulses emitted by the laser source. Such element is, for example, a prism, a grating or another acousto-optical deflector.

According to a preferred embodiment, the laser unit 18 also comprises a regenerative amplifier. A regenerative amplifier is a device which is used for obtaining a relatively strong amplification of optical pulses, usually with ultrashort pulse durations in the picosecond or femtosecond domain. In this embodiment, the laser unit 18 is thus adapted to provide optical pulses with relatively high intensity. For imaging applications, energy per pulse up to a few µJ are convenient.

The first optical system 20 is adapted to make the laser pulse emitted by the laser unit 18 going towards the shaping unit 22.

In the example of FIG. 1, the shaping unit 22 comprises four acousto-optical deflectors in series: a first acousto-optical deflector 36, a second acousto-optical deflector 38, a third acousto-optical deflector 40 and a fourth acousto-optical deflector 42.

Each acousto-optical deflector 36, 38, 40, 42 is adapted to deflect an incident laser pulse along a respective deflection direction to obtain a deflected laser pulse.

In this context, the expression "in series" refers to the fact that the input pulse of the subsequent acousto-optical deflector is the deflected pulse of the previous acousto-optical deflector.

Figure 2:
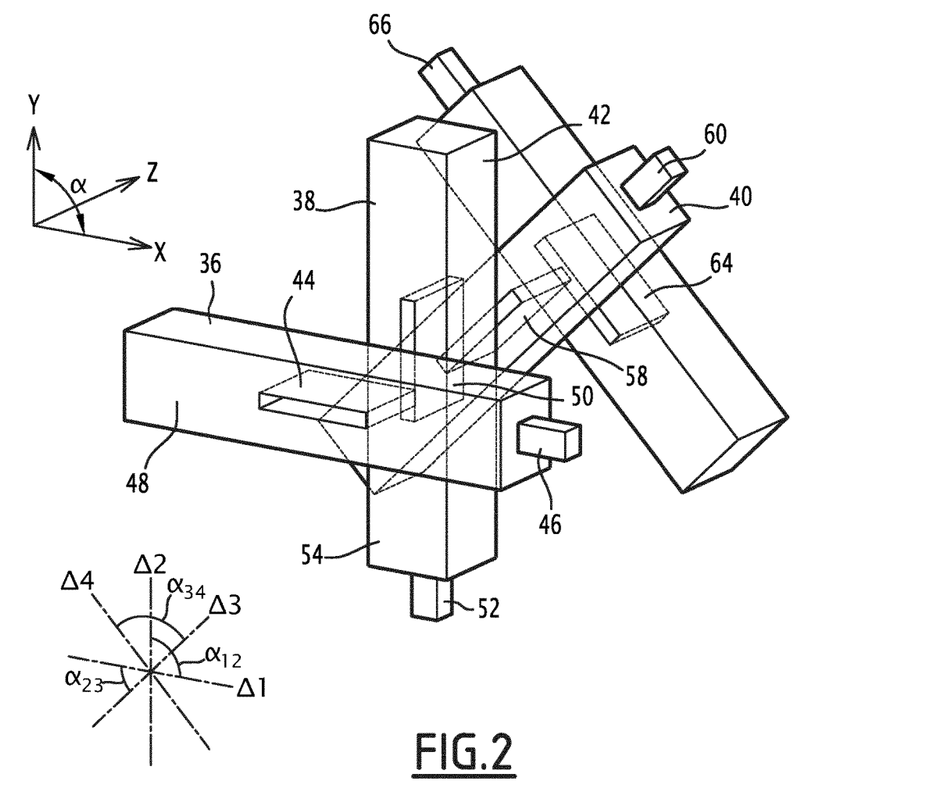
FIG. 2 is a perspective view of a part of the system for generating a spatial modulation of light of FIG. 1.
Figure 3:
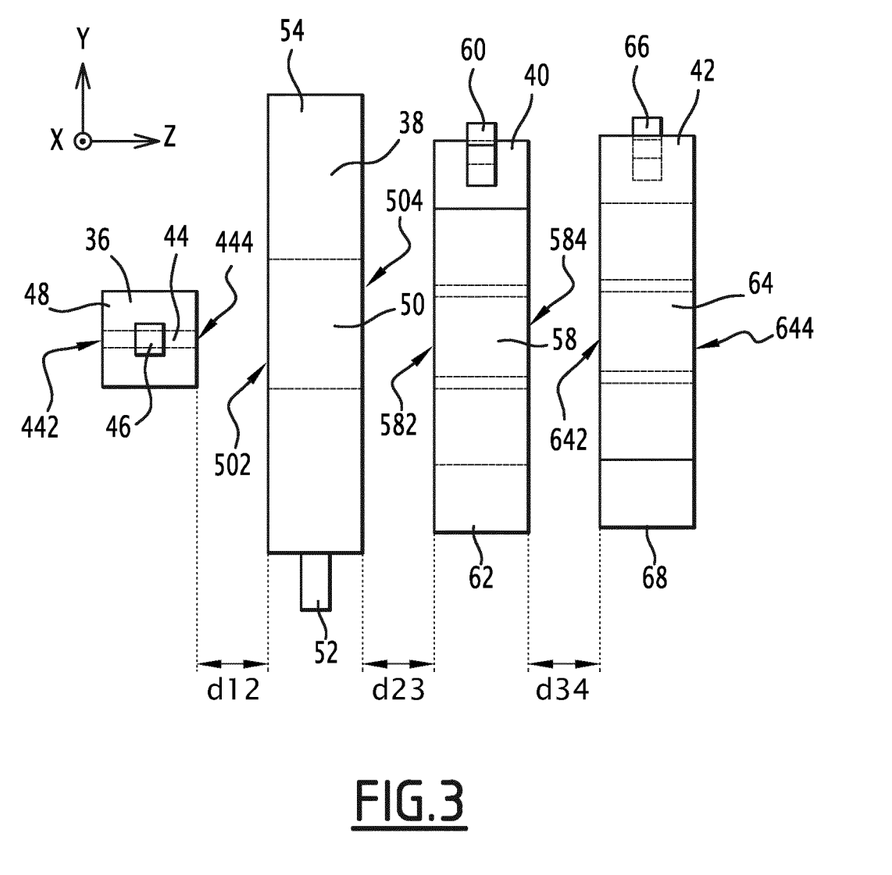
FIG. 3 is a side view of the part of the laser scanning unit represented in FIG. 2.

In FIG. 2, it appears that the first acousto-optical deflector 36 is adapted to deflect an input beam in the first deflection direction Δ1 to obtain a first deflected beam. The first deflection direction Δ1 is the first transverse direction X. In other words, the first acousto-optical deflector 36 is adapted to carry out a scan of the sample 12 in the first transverse direction X.

The first acousto-optical deflector 36 comprises a first acousto-optical crystal 44, a first transducer 46 and a first casing 48 protecting the first acousto-optical crystal 44.

The first acousto-optical crystal 44 has a parallelepipedic shape, the light entering by a first input face 442 and leaving by a first output face 444.

The distance between the first input face 442 and the first output face 444 along the longitudinal direction Z is the thickness of the crystal.

The first acousto-optical crystal 44 is a crystal made in $TeO_2$. Any other material exhibiting acousto-optical properties may be considered.

The first transducer 46 is adapted to command the first acousto-optical crystal 40 by applying a first acoustic wave. The variation of the properties of the first acoustic wave with time is according to a first law of command L1. Such properties comprise, for instance, the amplitude, the phase and the frequency of the first acoustic wave.

The first acousto-optical deflector 36 is further adapted to spatially shape the input laser pulse in phase and in amplitude according to a first complex function H1. It can be shown that the first function H1, due to the propagation velocity of the acoustic wave in the first acousto-optical crystal 40, can be expressed as a function of a coordinate along the first transverse direction X. For the remainder of the description, this coordinate is labeled x.

The second acousto-optical deflector 38 is adapted to deflect an input beam in the second deflection direction Δ2 to obtain a second deflected beam. The second deflection direction Δ2 is the second transverse direction Y. In other words, the second acousto-optical deflector 38 is adapted to carry out a scan of the sample 12 in the second transverse direction Y.

The angle between the first deflection direction Δ1 and the second deflection direction Δ2 is labeled the first angle $\alpha_{12}$. According to the example of FIG. 2, the first angle $\alpha_{12}$ is equal to 90°.

The second acousto-optical deflector 38 comprises a second acousto-optical crystal 50, a second transducer 52 and a second casing 54 protecting the second acousto-optical crystal 50.

The second acousto-optical crystal 50 has a parallelepipedic shape, the light entering by a second input face 502 and leaving by a second output face 504.

The distance between the second input face 502 and the second output face 504 along the longitudinal direction Z is the thickness of the crystal.

In the specific case illustrated, the second acousto-optical crystal 52 is identical to the first acousto-optical crystal 44.

The optical distance between the first acousto-optical crystal 44 and the second acousto-optical crystal 52 along the longitudinal direction Z is labeled first optical distance d12. By definition, the first optical distance d12 is the distance between the first output face 444 and the second input face 502 in the absence of optical relay system.

In case an optical relay system is present, this optical relay system images the first output face 444 into a conjugate plane and the optical distance d12 is the distance from this image plane to the second input face 502.

According an embodiment of the invention, the first optical distance d12 is inferior to 30 millimeters (mm).

According another embodiment of the invention, the first optical distance d12 is inferior to 15 millimeters (mm).

The second transducer 52 is adapted to command the second acousto-optical crystal 50 by applying a second acoustic wave. The variation of the properties of the second acoustic wave with time is according to a second law of command L2. Such properties comprise, for instance, the amplitude, the phase and the frequency of the second acoustic wave.

The second acousto-optical deflector 38 is further adapted to spatially shape the first deflected laser pulse in phase and in amplitude according to a second complex function H2. It can be shown that, due to the propagation velocity of the acoustic wave in the second acousto-optical crystal 50, the second function H2 can be expressed as a function of a coordinate along the second transverse direction Y. For the remainder of the description, this coordinate is labeled y.

The third acousto-optical deflector 40 is adapted to deflect an input beam in the third deflection direction Δ3 to obtain a third deflected beam. In other words, the third acousto-optical deflector 40 is adapted to carry out a scan of the sample 12 in the third transverse direction Δ3.

The angle between the second deflection direction Δ2 and the third deflection direction Δ3 is labeled the second angle $\alpha_{23}$. According to the example of FIG. 2, the second angle $\alpha_{23}$ is equal to 45°.

The third acousto-optical deflector 40 comprises a third acousto-optical crystal 58, a third transducer 60 and a third casing 62 protecting the third acousto-optical crystal 58.

The third acousto-optical crystal 58 has a parallelepipedic shape, the light entering by a third input face 582 and leaving by a third output face 584.

The distance between the third input face 582 and the third output face 584 along the longitudinal direction Z is the thickness of the crystal.

In the specific case illustrated, the third acousto-optical crystal 60 is identical to the first acousto-optical crystal 44.

The optical distance between the second acousto-optical crystal 50 and the third acousto-optical crystal 60 along the longitudinal direction Z is labeled second optical distance d23. By definition, the second optical distance d23 is the distance between the second output face 504 and the third input face 582 in the absence of optical relay system.

In case an optical relay system is present, this optical relay system images the second output face 504 into a conjugate plane and the optical distance d23 is the distance from this image plane to the third input face 582.

According an embodiment of the invention, the second optical distance d23 is inferior to 30 millimeters (mm).

According another embodiment of the invention, the second optical distance d23 is inferior to 15 millimeters (mm).

The third transducer 60 is adapted to command the third acousto-optical crystal 58 by applying a third acoustic wave. The variation of the properties of the third acoustic wave with time is according to a third law of command L3. Such properties comprise, for instance, the amplitude, the phase and the frequency of the third acoustic wave.

The third acousto-optical deflector 40 is further adapted to spatially shape the second deflected laser pulse in phase and in amplitude according to a third complex function H3. It can be shown that the third function H3, due to the propagation velocity of the acoustic wave in the third acousto-optical crystal 58, can be expressed as a function of a coordinate along the third deflection direction Δ3. For the remainder of the description, this coordinate is labeled x+y.

The fourth acousto-optical deflector 42 is adapted to deflect an input beam in the fourth deflection direction Δ4 to obtain a fourth deflected beam. In other words, the fourth acousto-optical deflector 42 is adapted to carry out a scan of the sample 12 in the fourth transverse direction Δ4.

The angle between the third deflection direction Δ3 and the fourth deflection direction Δ4 is labeled the third angle $\alpha_{34}$. According to the example of FIG. 2, the third angle $\alpha_{34}$ is equal to 90°.

The fourth acousto-optical deflector 42 comprises a fourth acousto-optical crystal 64, a fourth transducer 66 and a fourth casing 68 protecting the fourth acousto-optical crystal 64.

The fourth acousto-optical crystal 64 has a parallelepipedic shape, the light entering by a fourth input face 642 and leaving by a fourth output face 644.

The distance between the fourth input face 642 and the fourth output face 644 along the longitudinal direction Z is the thickness of the crystal.

In the specific case illustrated, the fourth acousto-optical crystal 66 is identical to the first acousto-optical crystal 44.

The optical distance between the third acousto-optical crystal 50 and the fourth acousto-optical crystal 66 along the longitudinal direction Z is labeled third optical distance d34. By definition, the third optical distance d34 is the distance between the third output face 584 and the fourth input face 642 in the absence of optical relay system.

In case an optical relay system is present, this images the third output face 584 into a conjugate plane and the optical distance d34 is the distance from this image plane to the fourth input face 642.

According an embodiment of the invention, the third optical distance d34 is inferior to 30 millimeters (mm).

According another embodiment of the invention, the third optical distance d34 is inferior to 15 millimeters (mm).

The fourth transducer 66 is adapted to command the fourth acousto-optical crystal 64 by applying a fourth acoustic wave. The variation of the properties of the fourth acoustic wave with time is according to a fourth law of command L4. Such properties comprise, for instance, the amplitude, the phase and the frequency of the fourth acoustic wave.

The fourth acousto-optical deflector 42 is further adapted to spatially shape the third deflected laser pulse in phase and in amplitude according to a fourth complex function H4. It can be shown that the fourth function H4, due to the propagation velocity of the acoustic wave in the fourth acousto-optical crystal 64, can be expressed as a function of a coordinate along the fourth deflection direction Δ4. For the remainder of the description, this coordinate is labeled y-x.

In an alternative embodiment, the acousto-optical crystal 44, 50, 58, 64 are in the same casing.

The radiofrequency generator 26 is adapted to provide, to each transducer 46, 52, 60 and 66, radiofrequency waves. Each transducer 46, 52, 60 and 66 is adapted to convert radiofrequency waves in an acoustic wave. Thus, the radiofrequency generator 26 is able to provide a first time-varying radiofrequency waves to the first transducer 46 corresponding to the first law of command L1. The radiofrequency generator 26 is also able to provide a second time-varying radiofrequency waves to the second transducer 52 corresponding to the second law of command L2. The radiofrequency generator 26 is also able to provide a third time-varying radiofrequency waves to the third transducer 60 corresponding to the third law of command L3. The radiofrequency generator 26 is also able to provide a fourth time-varying radiofrequency waves to the fourth transducer 66 corresponding to the fourth law of command L4.

The radiofrequency generator 26 is a direct digital synthesizer. Such device (whose usual acronym is DDS) is a type of frequency synthesizer used for creating arbitrary waveforms from a single, fixed-frequency reference clock.

Alternatively, the radiofrequency generator 26 is an analog system.

Preferably, the radiofrequency generator 26 is adapted to change the frequency between two values with a temporal jitter of the order of 10 ns or less, with a good phase continuity between the two values.

The second optical system 28 is adapted to serve as an optical relay between the output of the shaping unit 22 and the objective 32. The second optical system 28 is, for instance, a 4f relay.

The beam splitter 30 is adapted to reflect the light issued from the output of the shaping unit 22 towards the objective 32 and to transmit the light collected by the objective 32 to the detecting unit 16. For instance, the beam splitter 30 is a dichroic mirror.

The objective 32 is adapted to make the light received from the beam splitter 30 converge on a focal point situated in the vicinity of its focal plane located in the sample 12, to gather light emitted by the sample 12 and to send it to the beam splitter 32.

The controller unit 34 is adapted to synchronize the laser pulse unit 18 and the radiofrequency generator 26 such that each pulse emitted by the laser pulse unit 18 interacts with each acousto-optic deflectors 36, 38, 40 and 42 when each acoustic wave applied by the respective transducer 46, 52, 60 and 66 have the values enabling to obtain the desired spatial light modulation.

The detecting unit 16 comprises a third optical system 70 and a detector 72. The third optical system 70 is adapted to collect the light transmitted by the beam splitter 30 and to focus it on the detector 72. The detector 72 is adapted to convert the light received in an electrical signal. The detector 72 is, for instance, a photomultiplier.

Operation of the microscope 10 for two-photon imaging is now described when it is desired to obtain a desired pattern of light.

At a first instant t1, the radiofrequency generator 26 starts to apply a first radiofrequency wave to command the first acousto-optical deflector 36. The first transducer 46 converts the first radiofrequency wave into a first acoustic wave which propagates in the first crystal 44 and along axis X. This first acoustic wave has time-dependent amplitude and frequency, given by two first functions of time, with a continuity of the phase of the wave (these functions constitute together the first law of command L1). The resulting spatial profile of this first acoustic wave in the first crystal 36 at the time where the optical wave interacts with the first acousto-optical deflector 22, is such that the optical wave is spatially shaped in phase and in amplitude according to the first function H1. The establishment time of the first acoustic wave in the first crystal 44, that is the interval between the instant t1 when the acoustic wave command is generated and the instant $t1+t_{access,1}$ when the acoustic wave reaches the extremity opposite to the transducer of the optical window of the AOD, is referred as the access time $t_{access,1}$ of the first acousto-optical deflector 36. The access time notably depends from the size of the crystal along the axis X of propagation of the acoustic wave and from the frequency of the acoustic wave.

At a second instant t2, the radiofrequency generator 26 starts to apply a second radiofrequency wave to command the second acousto-optical deflector 38. The second transducer 52 converts the second radiofrequency wave into a second acoustic wave which propagates in the second crystal 50 and along axis Y. This second acoustic wave has time-dependent amplitude and frequency, given by two second functions of time, with a continuity of the phase of the wave (these functions constitute together the second law of command L2). The resulting spatial profile of this second acoustic wave in the second crystal 42 at the time where the optical wave interacts with the second acousto-optical deflector 24, is such that the optical wave is spatially shaped in phase and in amplitude according to the second function H2. The establishment time of the second acoustic wave in the second crystal 50, that is the interval between the instant t2 when the acoustic wave command is generated and the instant $t2+t_{access,2}$ when the acoustic wave reaches the extremity opposite to the transducer of the optical window of the AOD, is referred as the access time $t_{access,2}$ of the second acousto-optical deflector 38.

Both the precision in the determination of the first instant t1 and the precision in the determination of the second instant t2 are below or equal to 200 nanoseconds.

Preferably, the first instant t1 and the second instant t2 are chosen so that the first radiofrequency wave and the second radiofrequency wave are established simultaneously in the first and second acousto-optic deflectors ($t1+t_{access,1}=t2+t_{access,2}$).

The synchronization between the first instant t1 and the second instant t2 is carried out by the controller unit 34 and takes into account all the delays in the establishments of the two radiofrequency waves in the two acousto-optic deflectors.

At a third instant t3, the radiofrequency generator 26 starts to apply a third radiofrequency wave to command the third acousto-optical deflector 40. The third transducer 58 converts the third radiofrequency wave into a third acoustic wave which propagates in the third crystal 58 and along the third deflection direction Δ3. This third acoustic wave has time-dependent amplitude and frequency, given by two third functions of time, with a continuity of the phase of the wave (these functions constitute together the third law of command L3). The resulting spatial profile of this third acoustic wave in the third crystal 58 at the time where the optical wave interacts with the third acousto-optical deflector 40, is such that the optical wave is spatially shaped in phase and in amplitude according to the third function H3. The establishment time of the third acoustic wave in the third crystal 58, that is the interval between the instant t3 when the acoustic wave command is generated and the instant $t3+t_{access,3}$ when the acoustic wave reaches the extremity opposite to the transducer of the optical window of the AOD, is referred as the access time $t_{access,3}$ of the third acousto-optical deflector 40.

Both the precision in the determination of the second instant t2 and the precision in the determination of the third instant t3 are below or equal to 200 nanoseconds.

Preferably, the second instant t2 and the third instant t3 are chosen so that the second radiofrequency wave and the third radiofrequency wave are established simultaneously in the second and third acousto-optic deflectors. (t3+$t_{access,3}$=t2+$t_{access,2}$).

The synchronization between the second instant t2 and the third instant t3 is carried out by the controller unit 34 and takes into account all the delays in the establishments of the two radiofrequency waves in the two acousto-optic deflectors.

At a fourth instant t4, the radiofrequency generator 26 starts to apply a fourth radiofrequency wave to command the fourth acousto-optical deflector 42. The fourth transducer 66 converts the fourth radiofrequency wave into a fourth acoustic wave which propagates in the fourth crystal 64 and along fourth deflection direction Δ4. This fourth acoustic wave has time-dependent amplitude and frequency, given by two fourth functions of time, with a continuity of the phase of the wave (these functions constitute together the fourth law of command L4). The resulting spatial profile of this second acoustic wave in the second crystal 64 at the time where the optical wave interacts with the second acousto-optical deflector 42, is such that the optical wave is spatially shaped in phase and in amplitude according to the fourth function H4. The establishment time of the fourth acoustic wave in the fourth crystal 64, that is the interval between the instant t4 when the acoustic wave command is generated and the instant t4+$t_{access,4}$ when the acoustic wave-access reaches the extremity opposite to the transducer of the optical window of the AOD, is referred as the access time $t_{access,4}$ of the fourth acousto-optical deflector 42.

Both the precision in the determination of the third instant t3 and the precision in the determination of the fourth instant t4 are below or equal to 200 nanoseconds.

Preferably, the third instant t3 and the fourth instant t4 are chosen so that the third radiofrequency wave and the fourth radiofrequency wave are established simultaneously in the third and fourth acousto-optic deflectors (t4+$t_{access,4}$=t3+$t_{access,3}$).

The synchronization between the third instant t3 and the fourth instant t4 is carried out by the controller unit 34 and takes into account all the delays in the establishments of the two radiofrequency waves in the two acousto-optic deflectors.

At a fifth instant t5, the laser unit 18 emits a first laser pulse P1 towards the first optical system 20. The fifth instant t5 is posterior to the first instant t1.

Then, the first optical system 16 converts the first laser pulse P1 into a second laser pulse P2 whose waist is located in the first acousto-optical deflector 36. The second laser pulse P2 can thus be considered as the input laser pulse $P_{INPUT}$ for the first acousto-optical deflector 36. The input laser pulse $P_{INPUT}$ is also the input laser pulse $P_{INPUT}$ of the shaping unit 22.

The fifth instant t5 is more precisely chosen so that the second laser beam pulse P2 interacts with the first acousto-optical deflector 36 when the first acoustic wave is established in the first acousto-optical crystal 44. In other words, the interval of time between the first instant t1 and the fifth instant t5 is equal to the access time of the first acousto-optical deflector 36 (t5=t1+$t_{access,1}$). Therefore, the interval of time between the first instant t1 and the fifth instant t5 is comprised between 2 microseconds and 50 microseconds. A value A is comprised between a first value B and a second value C if the value A is superior or equal to the first value B and if the value A is inferior or equal to the second value C.

Such synchronization between the first instant t1 and the fifth instant t5 is carried out by the controller unit 34.

Both the precision in the determination of the first instant t1 and the precision in the determination of the fifth instant t5 are below or equal to 200 nanoseconds.

The first acousto-optical deflector 36 deflects the input laser pulse $P_{INPUT}$ or the second laser pulse P2 by a first angle of deviation in the first transverse direction first deflected pulse is labeled DP1. The first acousto-optical deflector 36 simultaneously spatially shapes the input laser pulse P2 in phase and amplitude in accordance with the first function H1.

The first deflected pulse DP1 propagates towards the second acousto-optical deflector 38. The second acousto-optical deflector 38 deflects the first deflected pulse DP1 by a second angle of deviation in the second transverse direction Y. This second deflected pulse is labeled DP2. The second acousto-optical deflector 38 simultaneously shapes spatially the first deflected laser pulse DP1 in phase and amplitude in accordance with the second function H2.

The second deflected pulse DP2 propagates towards the third acousto-optical deflector 40. The third acousto-optical deflector 40 deflects the second deflected pulse DP2 by a third angle of deviation in the third deflection direction Δ3. This third deflected pulse is labeled DP3. The third acousto-optical deflector 40 simultaneously shapes spatially the second deflected laser pulse DP2 in phase and amplitude in accordance with the third function H3.

The third deflected pulse DP3 propagates towards the fourth acousto-optical deflector 42. The fourth acousto-optical deflector 42 deflects the fourth deflected pulse DP4 by a fourth angle of deviation in the fourth deflection direction Δ4. This fourth deflected pulse is labeled DP4. The fourth acousto-optical deflector 42 simultaneously shapes spatially the third deflected laser pulse P3 in phase and amplitude in accordance with the fourth function H4.

The fourth deflected pulse DP4 is also the output laser pulse $P_{OUTPUT}$ of the shaping unit 22. The spatial modulation of the output laser pulse $P_{OUTPUT}$ is labeled $W_{OUTPUT}$.

The output laser pulse $P_{OUTPUT}$ then propagates towards the objective 32 via the second optical system 28 which serves as a relay and reflects on the beam splitter 30, so as to obtain a third laser pulse P3 at the back aperture of the objective whose spatial modulation W3 is similar to the spatial modulation $W_{OUTPUT}$ of the output laser pulse $P_{OUTPUT}$.

The objective 32 makes the third laser pulse P3 convergent near its focal plane located in the sample 12. By the expression "near", it is meant that the distance is inferior to 1 mm. The intensity distribution near the focal plane is determined by the spatial modulation W5.

More precisely, in the context of the invention, the spatial modulation W3 of the third laser pulse P3 enables to obtain by holography through the objective 32 the desired pattern of light in the image space of the objective 32.

As two-photon microscopy relies on the two-photon absorption phenomena predicted by Goeppert-Mayer in 1931, at each point of the light pattern, an interaction between the sample 12 and light occurs by simultaneous absorption of pairs of photons of the third laser pulse F3 by the sample 12. Following most of these biphotonic absorption events, the sample 12 emits one photon by fluorescence. The wavelength of the photon emitted is larger than half the wavelength of the photons of one pair.

The objective 32 then gathers fluorescence light emitted by the sample 12.

The beam splitter 30 transmits the fluorescence light towards the detecting unit 16.

The third optical system 72 makes the fluorescence light converge on the detector 72 which converts the fluorescence light in an electrical signal. This electrical signal contains information relative to the arrangement of sample 12 in space. Based on the electrical signal, a measure of the fluorescence intensity of the sample 12 at the position of the light pattern at this instant is achieved. Such measurement can be repeated over a given duration either at the same position, or over different discrete positions in two-dimension or three-dimension or over a set of continuous positions in two-dimension or three-dimension to analyze the sample 12.

Therefore, the system 14 for generating at least a desired spatial modulation of light enables to achieve an arbitrary pattern in a plane with a rate of up to 500 kHz. Indeed, at the time a pulse crosses one of the acousto-optical deflector 36, 38, 40, 42, this pulse interacts with a fixed acoustic grating generated by a controlled acoustic wave at the time it crosses each acousto-optical deflector 36, 38, 40, 42.

The properties of such acoustic waves with time, given by the laws of commands L1, L2, L3 and L4 are chosen to obtain the desired spatial modulation of the pulse. For this, for instance, the controller unit 34 determines the laws of commands L1, L2, L3 and L4 based on the desired spatial modulation of light. Such determination is achieved by using a method for determining the characteristics of the system 14. This method is further detailed below.

Furthermore, the system 14 is easy to implement since only four acousto-optical deflectors 36, 38, 40, 42 are involved. This results in a relatively high excitation power for the third laser pulse P3. Such high excitation power renders the system 14 together with an objective particularly adapted to produce non-linear effects, such as two-photon florescence absorption, second harmonic generation, third harmonic generation or coherent anti-Raman scattering. In addition such non-linear experiments may be carried out on highly scattering tissues at large depths.

Additionally, although the system 14 for generating at least a spatial modulation of light has been presented for an application related to two-photon fluorescence microscopy, the system 14 together with an objective can also be used for any measurement in the vicinity of its focal plane, such as transmission, fluorescence, refraction, polarization, scattering or reflection, or for any light-induced physical and/or chemical alteration of matter in the vicinity of the focal plane. In such cases, the beam splitter 30 may not be present and the detector unit 16 may be different.

According to another embodiment, the spatial modulation of light evolves with time. In this case, several laser pulses are emitted by the laser unit 18 at a repetition rate. Such repetition rate should be inferior or equal to the inverse of the largest of the access times of each acousto-optic deflectors 36, 38, 40, 42.

According to another embodiment, as the output laser pulse has a spatial and/or temporal dispersion, the system 14 comprises a unit for compensating for the spatial and/or temporal dispersion. Such unit for compensating for the spatial and/or temporal dispersion is, for instance, a prism, a grating or a pair of prisms or gratings.

To determine the four laws of command L1, L2, L3, L4 a method for determining the characteristics of a system 14 is proposed.

The method for determining comprises a step of providing the desired spatial modulation of light.

The method for determining also comprises a step of expressing the amplitude and the phase of the output pulse $P_{OUTPUT}$ of the shaping unit 22 as a function of the input laser pulse $P_{INPUT}$ and in function of the characteristics of the system 14 to obtain a calculated output pulse.

This step of expressing enables to express the operating of the shaping unit 22 in term of a global transfer function converting the input laser pulse $P_{INPUT}$ in the output pulse $P_{OUTPUT}$.

For this, according to a preferred embodiment, the global transfer function of the shaping unit 22 is obtained by considering the transfer function of each acousto-optical deflector 36, 38, 40, 42. By definition, the transfer function of an acousto-optical deflector is a link between the input laser pulse in the acousto-optical deflector and the deflected laser pulse.

Such transfer function is calculated by using a relationship between the frequency and amplitude pattern in the considered acousto-optical deflector and the spatial modulation in phase and in amplitude of the deflected laser pulse.

Notably, for each acousto-optical deflector 36, 38, 40, 42, the phase shift introduced by the acousto-optical deflector 36, 38, 40, 42 between the deflected laser pulse and the incident laser pulse is expressed, according to the formula 1, as:

$$\varphi(m) = \frac{2\pi}{v}\left(mf(m) - m_0 f(m_0) - \int_{m_0}^{m} uf'(u)du\right)$$

wherein:
  φ is the phase shift introduced by the acousto-optical deflector 36, 38, 40, 42 in the incident laser pulse,
  m is the coordinate of the position of a point of the acousto-optical crystal 44, 50, 58, 64 along the deflection direction Δ1, Δ2, Δ3 and Δ4,
  $m_0$ is the coordinate of the position of an extremity of the acousto-optical crystal 44, 50, 58, 64 along the deflection direction Δ1, Δ2, Δ3 and Δ4,
  v is the speed of the acoustic wave applied to the crystal of the acousto-optical deflector 36, 38, 40, 42, and
  f(m) is the frequency of the acoustic wave applied to the crystal 44, 50, 58, 64 of the acousto-optical deflector 36, 38, 40, 42 at the point of coordinate m.

The amplitude modulation introduced by the acousto-optical deflector between the deflected laser pulse and the incident laser pulse is expressed as:

$$A(m) = T(a(m))$$

wherein:
  A(m) is the amplitude modulation introduced by the acousto-optical deflector in the incident laser pulse,
  m is the coordinate of the position of a point of the acousto-optical crystal along the deflection direction,
  a(m) is the amplitude of the acoustic wave applied to the crystal of the acousto-optical deflector at the point of coordinate m, and
  T is the characteristic input-output amplitude transfer function of the acousto-optical deflector (36, 38, 40, 42) expressing the fraction of the input light amplitude transferred into the first diffraction order, as a function of the acoustic wave amplitude.

Such expression is explained for the first acousto-optical deflector 36, the same reasoning applying to the other acousto-optical deflectors 38, 40, 42.

Let's consider an incident pulse propagating along the longitudinal direction Z and interacting with the first acousto-optical deflector 36.

Thus, the amplitude of the incident pulse can be expressed as:

$$A_{in}(x,y,z) = A_{in}(x,y)e^{i(k_0z + \varphi_0(x,y))}$$

where:
- $f(m_0)$ is generated at times t1, t2, t3, t4,
- $f(m)$ is generated at times $t1+(m-m_0)/v$, $t2+(m-m_0)/v$, $t3+(m-m_0)/v$, $t4+(m-m_0)/v$
- $\varphi(m)$ is obtained at one of the times $t1+t_{access,1}$, $t2+t_{access,2}$, $t3+t_{access,3}$, $t4+t_{access,4}$, which are equal within a precision of less than 200 ns, and where:
- $A_{in}(x,y,z)$ is the amplitude of the incident pulse,
- z is the coordinate along the longitudinal axis Z,
- $k_o$ is the propagation constant of the incident pulse,
- $A_{in}(x,y)$ is the incident amplitude profile of the incident pulse. The amplitude profile is, for instance, planar or Gaussian.
- $\varphi_0(x,y)$ is the incident wavefront of the incident pulse. Preferably, the incident wavefront $\varphi_0(x,y)$ is planar for optimizing diffraction efficiency in the acousto-optical crystal 58.

When the first acousto-optical deflector 36 is fed with an ultrasonic wave with frequency f(x) and amplitude a(x) at a position x in the first acousto-optical deflector 36, after interaction, the amplitude of the deflected pulse can be expressed as:

$$A_{out}(x,y,z) = A_{in}(x,y) \cdot T_1(a_1(x))e^{i(k_0z + \varphi_0(x,y) + \varphi_1(x))}$$

Where:
- $A_{out}(x,y,z)$ is the amplitude of the deflected pulse,
- $T_1$ is the characteristic input-output amplitude transfer function of the first acousto-optical deflector 36 expressing the fraction of the input light amplitude transferred into the first diffraction order, as a function of the acoustic wave amplitude $a_1$, and
- $\varphi_1(x,y)$ is the phase shift introduced by the first acousto-optical deflector 36 between the deflected laser pulse and the incident laser pulse.

The phase shift introduced by the first acousto-optical deflector 36 between the deflected laser pulse and the incident laser pulse $\varphi_1(x,y)$ is related to the frequency f(x) of the ultrasonic wave in a complex manner.

At each point x of the AOD, the rays are diffracted in a direction given by:

$$\theta(x) = \frac{\lambda f(x)}{v}$$

At any point x, the rays coming out of the first acousto-optical deflector 36 are perpendicular to the wavefront. Therefore, the optical path difference between the position x and x+dx of the wavefront due to the angle θ(x) of the rays at the coordinated x, is θ(x).dx and the wavefront is therefore related to the frequency in the AOD by:

$$\frac{d\phi_1(x)}{dx} = \frac{2\pi}{\lambda}\theta(x) = \frac{2\pi f(x)}{v}$$

This can be written as the following equations:

$$\phi_1(x) = \frac{2\pi}{v}\int_{x0}^{x} f(u)du$$

$$\phi_1(x) = \frac{2\pi}{v}\left[uf(u)\right]_{x0}^{x} - \int_{x0}^{x} uf'(u)du$$

$$\phi_1(x) = \frac{2\pi}{v}\left(xf(x) - x_0 f(x_0) - \int_{x0}^{x} uf'(u)du\right)$$

where $x_0$ is the coordinate of the position of the extremity opposite to the transducer of the optical window of the first acousto-optical crystal 44 along the first transverse direction X.

In this expression $f(x_0)$ is generated at time t1, f(x) is generated at time $t1+(x-x_0)/v$, and $\varphi(x)$ is obtained at time $t1+t_{access,1}$, $t_{access,1}$ being the access time of the first acousto-optic deflector, i.e. the interval between the instant t1 when the acoustic wave command is generated and the instant $t1+t_{access,1}$ when the acoustic wave reaches the extremity opposite to the transducer of the optical window of the first acousto-optic deflector, The last formula is called formula 1 in the remainder of the specification.

This expression shows that the phase profile created at a position x, for a single acousto-optical deflector cannot be related only to the ultrasonic frequency at the pixel x in the acousto-optical deflector but is related to the whole ultrasonic pattern from an extremity to the point x.

By applying successively formula 1 to each acousto-optical deflector 36, 38, 40, 42, the global transfer function of the shaping unit 22 is obtained. Such global transfer function depends from the four laws of command L1, L2, L3, L4.

Then, for a given input pulse $P_{INPUT}$, a calculated output pulse $P_{OUTPUT}$ which depends from the four laws of command L1, L2, L3, L4 is obtained.

The method for determining also comprises a step of determining the four laws of command L1, L2, L3, L4 to apply to the system 12 by minimizing a distance between the calculated output pulse $P_{OUTPUT}$ spatial modulation and the desired output laser pulse spatial modulation.

The distance should be understood as meaning a quantification of the difference between the calculated output pulse $P_{OUTPUT}$ spatial modulation and the desired output laser pulse spatial modulation.

Thus, any mathematical norm may be used in this context.

Such minimizing step is, for instance, carried out by using a damped least squares technique. In such case, the distance is the Euclidean distance.

According to another embodiment, the distance is the difference between the intensity obtained with the calculated output pulse $P_{OUTPUT}$ spatial modulation and the intensity obtained with the desired output laser pulse spatial modulation.

Such method for determining enables to determine the four laws of command L1, L2, L3, L4 to apply to the system 12, for the system 12 to be able to generate a given spatial light modulation.

Such method for determining applies for any characteristic of the system 12. For instance, the characteristics are chosen in the group consisting of the optical distances between the acousto-optical deflectors, the angles between the deflection direction and the number of acousto-optical deflectors.

Such method for determining is usable in any configuration of acousto-optical deflectors.

As a first example, the case of two acousto-optical deflectors with their two deflection directions being perpendicular can be considered. This corresponds to the case of FIG. 2 without the third and the fourth acousto-optical deflectors. Such configuration is a crossed configuration. The phase modulation is of the form $\varphi_1(x)+\varphi_2(y)$ and the amplitude modulation of the form $T_1(a_1(x))\cdot T_2(a_2(y))$. This configuration can create only phase and amplitude spatial modulations having the following functional form:

$$T_1(a_1(x))\cdot T_2(a_2(y))\exp[i(\varphi_1(x)+\varphi_2(y))]$$

More complex spatial modulation can only be approximated, as for instance, spatial phase modulation having cross term $x^a y^b$ where a and b are numbers different from zero.

In the case of more complex spatial modulations, as a second example, let's consider N acousto-optical deflectors (N being an integer strictly superior to 2), whose deflection directions are equally spaced angularly.

In such second example, each acousto-optical deflector has an amplitude modulation $T_i(a_i(x))$ and a phase shift $\varphi_i(x)$ related to the frequency $f_i(x)$ in the i-th acousto-optical deflector as described in reference to formula 1. Due to the spatial arrangement of the N acousto-optical deflectors, the amplitude modulation introduced by the shaping unit 22 is of the form $$\Pi_{i=0}^{N-1} T_i(a_i)\left(\cos\left(\frac{i\pi}{N}\right)x + \sin\left(\frac{i\pi}{N}\right)y\right)$$

and the phase modulation introduced by the shaping unit 22 is of the form $$\sum_{i=0}^{N-1} \varphi_i\left(\cos\left(\frac{i\pi}{N}\right)x + \sin\left(\frac{i\pi}{N}\right)y\right).$$

Such second example allows the user to better approximate a spatial light modulation at the expense of laser power due to the energy losses in the acousto-optical deflectors.

The example of FIG. 2 is a specific case of the second example wherein N=4. In this example, the system 14 is able to produce a spatial modulation with a phase shift corresponding to the sum of four terms. Each term is respectively a function of x (for first acousto-optical deflector 36), y (for second acousto-optical deflector 38), x+y (for third acousto-optical deflector 40) and y−x (for fourth acousto-optical deflector 42).

According to preferred embodiments, the step d) is carried out by using a constraint or a combination of constraint.

For instance, according to a constraint, the number of acousto-optical deflectors is strictly superior to 2.

According to another constraint, the first instant t1 and the second instant t2 are controlled with a precision below or equal to 200 nanoseconds. This constraint can be generalized as the interval of time between the instant when a radiofrequency wave is established in one acousto-optic deflector and the instant when a radiofrequency wave is established in a subsequent acousto-optic deflector is below or equal to 200 nanoseconds.

According to another constraint, the interval of time between the instant when a radiofrequency wave is established in one acousto-optic deflector and the instant when a radiofrequency wave is established in a subsequent acousto-optic deflector is equal to zero (ti+$t_{access,1}$=tj+$t_{access,j}$, for i=1 to 4 and for j=1 to 4).

According to another constraint, the fifth instant t5 is posterior to the first instant t1.

According to another constraint, each acousto-optic deflector has an access time, the repetition rate of the laser unit be inferior or equal to the inverse of the largest of these access times.

The method for determining therefore enables to obtain the characteristics of a system enabling to generate an arbitrary spatial light modulation at high speed. This high speed of the order of hundreds of kHz range is not achievable by any known technology. Indeed beam shaping has been achieved using a great variety of technologies including deformable mirrors (DM), liquid crystal Spatial Light Modulators (SLM) or MEMS mirrors. Most of these techniques are limited to a refresh rate of a few Hz, up to a few kHz Such high speed is all the more important as the shaping of a laser beam, which consists in the spatial modulation of its phase and amplitude, has major applications in various fields including materials processing (micro-photolithography, laser writing, laser welding, hole drilling, laser ablation, laser scribing), laser displays, optical communication, medicine and optical microscopy. Whereas static spatial shaping is often achieved, the ability to change the beam shape at high rate can be of great importance to improve the throughput of all these applications.

In addition, such method for determining can be carried out easily and notably by making a computing system and a computer program product interact.

The computing system is, for instance, a computer. More generally, the computing system is a computer or similar electronic computing device adapted to manipulate and/or transform data represented as physical, such as electronic, quantities within the computing system's registers and/or memories into other data similarly represented as physical quantities within the computing system's memories, registers or other such information storage, transmission or display devices.

Computing system comprises a processor, a keyboard and a display unit.

The processor comprises a data-processing unit, memories and a reader adapted to read a computer readable medium.

The computer program product comprises a computer readable medium.

The computer readable medium is a medium that can be read by the reader of the processor. The computer readable medium is a medium suitable for storing electronic instructions, and capable of being coupled to a computer system bus.

Such computer readable storage medium is, for instance, a disk, a floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A computer program is stored in the computer readable storage medium. The computer program comprises one or more stored sequence of program instructions.

The computer program is loadable into the data-processing unit and adapted to cause execution of the method for determining when the computer program is run by the data-processing unit.

The embodiments and alternative embodiments considered here-above can be combined to generate further embodiments of the invention.

The invention claimed is:

1. Method for determining the characteristics of a system for generating a desired spatial light modulation in phase and in amplitude of a laser pulse, the system comprising:
   a laser unit adapted to emit at least one input laser pulse having a duration below or equal to 1 nanosecond,
   a spatial shaping unit being adapted to generate an output laser pulse when illuminated by an input laser pulse, the spatial shaping unit comprising at least one acousto-optical deflector, each acousto-optical deflector being adapted to deflect an incident laser pulse along a respective deflection direction to obtain a deflected laser pulse, each acousto-optical deflector comprising an acousto-optical crystal and a transducer adapted to command the crystal by applying an acoustic wave,
   the laser unit and the shaping unit being synchronized such that the incident laser pulse interacts with the respective acousto-optic deflector when the acoustic wave is established in the crystal,
   the method comprising:
   a) providing a desired spatial light modulation in phase and in amplitude of the output pulse,
   b) expressing the amplitude and the phase of the output pulse of the shaping unit as a function of the input laser pulse and in function of the characteristics of the system to obtain a calculated output pulse,
   wherein:
   the method further comprises:
   c) determining at least one characteristic of the system by minimizing a distance between the calculated output pulse and the desired output laser pulse,
   at step b), for each acousto-optical deflector, the phase shift introduced by the acousto-optical deflector between the deflected laser pulse and the incident laser pulse is expressed as:

$$\varphi(m) = \frac{2\pi}{v}\left(mf(m) - m_0 f(m_0) - \int_{m_0}^{m} uf'(u)du\right)$$

wherein:
   $\varphi$ is the phase shift introduced by the acousto-optical deflector in the incident laser pulse,
   m is the coordinate of the position of a point of the acousto-optical crystal along the deflection direction,
   $m_0$ is the coordinate of the position of the extremity of the acousto-optical crystal along the deflection direction and opposite to the transducer,
   v is the speed of the acoustic wave applied to the crystal of the acousto-optical deflector, and
   f(m) is the frequency of the acoustic wave applied to the crystal of the acousto-optical deflector at the point of coordinate m at the instant when the laser pulse crosses the crystal, and
   $t_{access}$ being the access time of the acousto-optic deflector, and
   at step b), for each acousto-optical deflector, the amplitude modulation introduced by the acousto-optical deflector between the deflected laser pulse and the incident laser pulse is expressed as:

$$A(m)=T(a(m))$$

wherein:
   A(m) is the amplitude modulation introduced by the acousto-optical deflector in the incident laser pulse at the point of coordinate m,
   a(m) is the amplitude of the acoustic wave applied to the crystal of the acousto-optical deflector at the point of coordinate m at the instant when the laser pulse crosses the crystal, and
   T is the characteristic input-output amplitude transfer function of the acousto-optical deflector expressing the fraction of the input light amplitude transferred into the first diffraction order, as a function of the acoustic wave amplitude.

2. A method according to claim 1, wherein the shaping unit comprises at least two acousto-optical deflectors in series, the number of acousto-optical deflectors being a characteristic of the system and being determined at step c) under the constraint that the number of acousto-optical deflectors be superior or equal to 2, preferably superior or equal to 4.

3. A method according to claim 1, wherein each characteristic determined at step c) is determined under the constraint that the deflection directions are equally spaced angularly.

4. A method according to claim 1, wherein the system further comprises a radiofrequency generator adapted to provide to each transducer radiofrequency wave starting at a respective instant, the instants being characteristics of the system and being determined at step c).

5. The method according to claim 1, wherein the system further comprises a laser unit adapted to emit laser pulse at emitting instants, the emitting instants being a characteristic of the system and each acousto-optic deflector has an access time, the emitting instants being determined at step c) under the constraint that the repetition rate of the laser unit be inferior or equal to the inverse of the largest of these access times.

6. The method according to claim 1, wherein the characteristics are chosen in the group consisting of the optical distances between the acousto-optical deflectors, the angles between the deflection directions and the number of acousto-optical deflectors.

7. Computer program product comprising a computer readable medium, having thereon a computer program comprising program instructions, the computer program being loadable into a data-processing unit and adapted to cause execution of a method according to claim 1 when the computer program is run by the data-processing unit.

8. System for generating a desired spatial modulation in phase and in amplitude of a laser pulse, the system comprising: a laser unit adapted to emit at least one input laser pulse having a duration below or equal to 1 nanosecond,
   a shaping unit being adapted to generate an output laser pulse when illuminated by an input laser pulse, the shaping unit comprising at least one acousto-optical deflector, each acousto-optical deflector being adapted to deflect an incident laser pulse along a respective deflection direction to obtain a deflected laser pulse, each acousto-optical deflector comprising an acousto-optical crystal and a transducer adapted to command the crystal by applying an acoustic wave,
   the laser unit and the shaping unit being synchronized such that the incident laser pulse interacts with the respective acousto-optic deflector when the acoustic wave is established in the crystal, wherein the system has at least a characteristic determined by the method for determining according to claim 1.

9. System according to claim 8, wherein the laser unit comprises a laser and a regenerative amplifier.

10. A two-photon microscope comprising a system for generating a desired laser pulse according to claim 8.

11. Method of generating a desired spatial modulation in phase and in amplitude of a laser pulse by using the system for generating at least a desired laser pulse according to claim 8.

12. Method for analyzing or modifying a sample comprising generating a light pattern within a sample by using the method for generating at least a desired spatial modulation in phase and in amplitude of a laser pulse according to claim 11.

13. Method for analyzing or modifying a sample according to claim 12 comprising modifying the position of the pattern of light in the sample along a direction perpendicular to the focal plane.

14. A method for analyzing or modifying a sample according to claim 12, wherein the sample is adapted to tolerate an exposition to a maximum repartition of intensity of light in the focal plane, the method further comprising choosing the desired pattern of light so that the repartition of the intensity of the desired pattern of light in the focal plane be inferior to the maximum repartition of intensity.

* * * * *